United States Patent [19]

Alig et al.

[11] 4,029,692

[45] June 14, 1977

[54] STEROID CARBOXYLIC ACIDS AND DERIVATIVES

[76] Inventors: Leo Alig, 76 Heidenlochstrasse, Liestal, Switzerland; Robert Nickolson, 102 Mohriner Allee; Rudolf Wiechert, 5 Petzower-Strasse, both of Berlin, Germany; Andor Fürst, 14 Magnolienpark, Basel, Switzerland; Klaus Kieslich, 4 Strasse zum Lowen, Berlin, Germany; Marcel Müller, 10 Quellenweg, Frenkendorf, Switzerland; Ulrich Kerb, 8 Waitzstrasse, Berlin, Germany

[22] Filed: Mar. 29, 1976

[21] Appl. No.: 671,381

[30] Foreign Application Priority Data

Apr. 3, 1975 Switzerland ............... 4224/75
Jan. 30, 1976 Switzerland ............... 1172/76
Mar. 22, 1976 Switzerland ............... 3507/76

[52] U.S. Cl. ..................... 260/468.5; 260/410; 260/468 R; 260/476 C; 260/488 B; 260/514.5; 424/305; 424/308; 424/311; 424/312; 424/317

[51] Int. Cl.² ............... C07C 69/74; C07C 61/36; C07C 69/16; C07C 69/28
[58] Field of Search ......... 260/468.5, 488 B, 514.5, 260/468 R, 476 C, 410

[56] References Cited

UNITED STATES PATENTS 2,880,233   3/1959   Clinton ..................... 260/488 B
3,939,193   2/1976   Alig ........................ 260/488 B

OTHER PUBLICATIONS

"Elseviers Encyclopeadia of Organic Chemistry," vol. 14 supp., pp. 3379s, 3384s, 3440s, 3441s, 3497s & 3498s (1962).

Primary Examiner—Lorraine A. Weinberger
Assistant Examiner—Michael Shippen
Attorney, Agent, or Firm—Samuel L. Welt; George M. Gould

[57] ABSTRACT

The present disclosure relates to steroid carboxylic acids and derivatives thereof. More particularly, the disclosure is concerned with D-homosteroid carboxylic acids and their derivatives, a process for the preparation thereof and pharmaceutical compositions containing same. The instant compounds are active endocrinal agents, especially as antiinflammatory agents.

43 Claims, No Drawings

STEROID CARBOXYLIC ACIDS AND DERIVATIVES

DISCLOSURE OF THE INVENTION

The D-homosteroid carboxylic acids and their derivatives provided by the present invention have the following formula

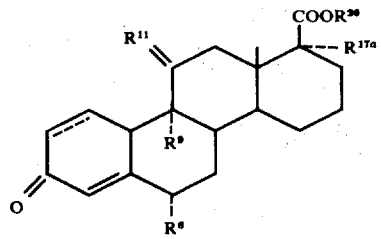

wherein $R^6$ is a hydrogen, fluorine, chlorine or methyl group; $R^9$ is hydrogen, fluorine, chlorine or bromine; $R^{11}$ is oxo or ($\alpha$-H, $\beta$-OH) when $R^9$ is hydrogen or oxo, ($\alpha$-H, $\beta$-OH), ($\alpha$-H, $\beta$-fluoro) or ($\alpha$-H, $\beta$-chloro) when $R^9$ is fluorine, chlorine or bromine with the proviso that, in the case of 9,11-dihalo compounds, the atomic number of the halogen atom in the 9-position is not less than the atomic number of the halogen atom in the 11-position; $R^{17a}$ is hydroxy or acyloxy and $R^{20}$ is hydrogen, lower alkyl, halo-(lower alkyl), hydroxy-(lower alkyl), acyloxy-(lower alkyl) or (lower alkoxycarbonyl)-(lower alkyl) and the broken line in the 1,2-position denotes an optional carbon-carbon bond.

An acyloxy group can be derived from a saturated or unsaturated aliphatic carboxylic acid, a cycloaliphatic, araliphatic or an aromatic carboxylic acid preferably containing up to 15 carbon atoms. Examples of such acids are formic acid, acetic acid, pivalic acid, propionic acid, butyric acid, caproic acid, oenanthic acid, undecylenic acid, oleic acid, cyclopentylpropionic acid, cyclohexylpropionic acid, phenylacetic acid and benzoic acid. Especially preferred acyloxy groups are alkanoyloxy groups containing from 1 to 7 carbon atoms. Lower alkyl groups can be straight-chain or branched-chain and can contain 16 carbon atoms. Especially preferred lower alkyl groups are those containing from 1 to 4 carbon atoms, especially a methyl or ethyl group. The lower alkyl moieties of the halo-(lower alkyl), hydroxy-(lower alkyl), acyloxy-(lower alkyl) and (lower alkoxycarbonyl)-(lower alkyl) groups have the same significance. The term "halo" includes fluoro, chloro, bromo and iodo unless not expressly defined to the contrary. Examples of halo-(lower alkyl) groups are fluoromethyl, chloromethyl, bromomethyl, $\beta$-fluoroethyl, $\beta$-chloroethyl and $\beta$-bromoethyl. An example of a hydroxy-(lower alkyl) group is the $\beta$-hydroxyethyl group and an example of an acyloxy-(lower alkyl) group is the $\beta$-acetoxyethyl group. A (lower alkoxycarbonyl)-(lower alkyl) group may be, for example, the methoxycarbonylmethyl group.

In the case 9,11-dihalo-D-homosteroids of formula I, the halogen atom in the 11-position should have a lower atomic weight or the same atomic weight as the halogen atom in the 9-position. In the case of D-homosteroids of formula I in which $R^9$ is hydrogen, $R^{11}$ can only be oxo or ($\alpha$-H, $\beta$-OH).

A preferred group of D-homosteroids of formula I comprises those in which $R^{11}$ is ($\alpha$-H, $\beta$-OH). Furthermore, those D-homosteroids of formula I in which $R^9$ is hydrogen, fluorine or chlorine are preferred. D-Homosteroids of formula I containing a double band in the 1,2-position are also preferred.

Examples of D-homosteroids of formula I are:
11$\beta$,17a$\alpha$-Dihydroxy-3-oxo-D-homoandrost-4-ene-17a$\beta$-carboxylic acid,
11$\beta$, 17a$\beta$-dihydroxy-3-oxo-D-homoandrosta-1,4-diene-17a$\beta$-carboxylic acid,
9$\alpha$-fluoro-11 $\beta$, 17a $\alpha$-dihydroxy-3-oxo-D-Homoandrost-4-ene-17a $\beta$-carboxylic acid,
9$\alpha$-fluoro-11$\beta$, 17a $\alpha$-dihydroxy-3-oxo-D-homoandrosta-1,4-diene-17a $\beta$-carboxylic acid,
6$\alpha$,9$\alpha$-difluoro-11$\beta$,17a $\alpha$,-dihydroxy-3-oxo-D-homoandrost-4-ene-17a$\beta$-carboxylic acid,
6$\alpha$, 9$\alpha$-difluoro-11$\beta$, 17a$\alpha$-dihydroxy-3-oxo-D-homoandrosta-1,4-diene-17a $\beta$-carboxylic acid,
6$\alpha$-chloro-11$\beta$, 17a$\alpha$-dihydroxy-3-oxo-D-homoandrost-4-ene-17a $\beta$-carboxylic acid,
6$\alpha$-chloro-9$\alpha$-fluoro-11$\beta$, 17a$\alpha$-dihydroxy-3-oxo-D-homoandrost-4-ene-17a$\beta$-carboxylic acid,
6$\alpha$-chloro-9$\alpha$-fluoro-11$\beta$, 17a$\alpha$-dihydroxy-3-oxo-D-homoandrosta-1,4-diene-17a$\beta$-carboxylic acid,
11$\beta$,17a$\alpha$-dihydroxy-6$\alpha$-methyl-3-oxo-D-homoandrost-4-ene-17a$\beta$-carboxylic acid,
9$\alpha$, 11$\beta$-dichloro-17a$\alpha$-hydroxy-3-oxo-D-homoandrost-4-ene-17a$\beta$-carboxylic acid,
9$\alpha$, 11$\beta$-dichloro-17a$\beta$-hydroxy-3-oxo-D-homoandrosta-1,4-diene-17a$\beta$-carbosylic acid,
6$\alpha$, 9$\alpha$-dichloro-11$\beta$-fluoro-17a$\alpha$-hydroxy-3-oxo-D-homoandrost-4-ene-17a $\beta$-carboxylic acid,
6$\alpha$, 9$\alpha$-dichloro-11$\beta$-fluoro-17a$\alpha$-hydroxy-3-oxo-D-homoandrosta-1,4 -diene-17a$\beta$-carboxylic acid,
the methyl, ethyl, propyl and butyl esters of these compounds as well as the 17a$\alpha$-acetates, propionates and butyrates; for example, 17a$\alpha$-acetoxy-9$\alpha$-fluoro-11$\beta$-hydroxy-3-oxo-D-homoandrosta-1,4-diene-17a$\beta$-carboxylic acid methyl ester.

The D-homosteroids of formula I hereinbefore are prepared by a. dehydrogenating a 1,2-saturated D-homosteroid of formula in the 1,2-position or b. oxidising the 3-hydroxy-$\Delta^5$ grouping in a D-homosteroid of the formula

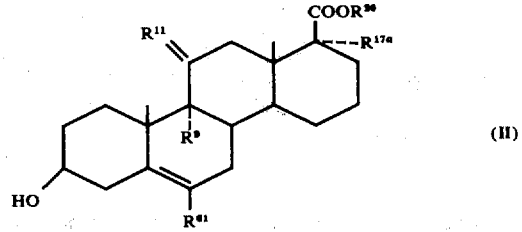

to the 3-keto-$\Delta^4$ grouping, or c. fluorinating or chlorinating a D-homosteroid of the general formula

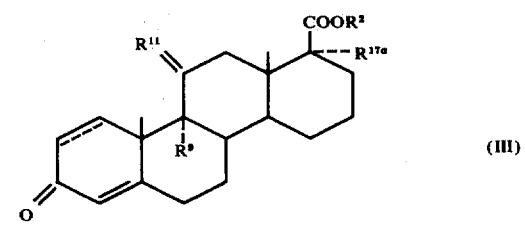

in the 6-position and, if desired, isomerising a 6β-isomer obtained to the 6α-isomer, or d. methylating a D-homosteroid of the general formula

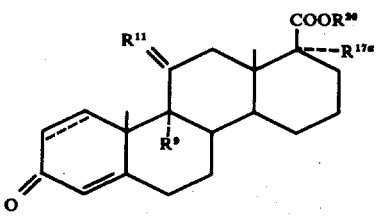

in the 6-position or e. subjecting a D-homosteroid of the general formula

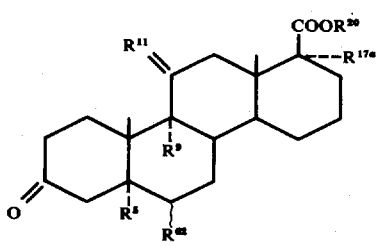

to a HR⁵-cleavage, or f. adding chlorine, ClF, BrF, BrCl, hypochlorous acid or hypobromous acid to the 9,11-double bond of a D-homosteroid of the general formula

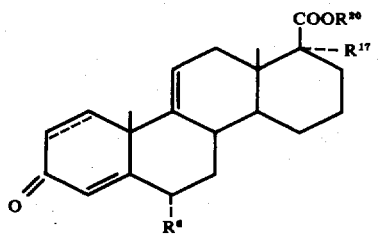

or g. treating a D-homosteroid of the general formula

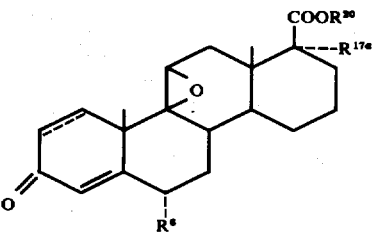

with hydrogen fluoride, hydrogen chloride or hydrogen bromide, or h. hydroxylating a D-homosteroid of the general formula

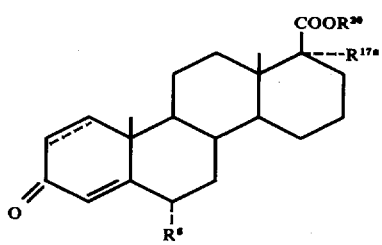

in the 11-position by means of microorganisms or enzymes obtained therefrom, or i. reducing the 11-keto group in a D-homosteroid of the general formula

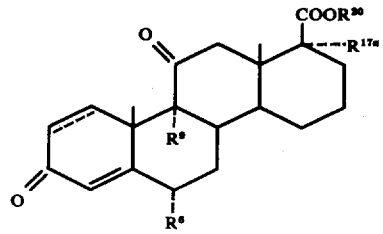

to the 11β-hydroxy group, or j. oxidising the 11-hydroxy group in a D-homosteroid of the general formula

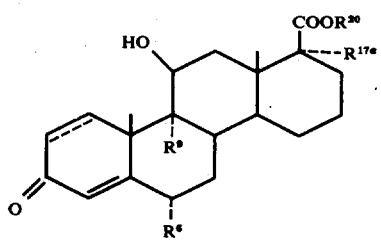

to the keto group, or k. acylating the 17aα-hydroxy group in a D-homosteroid of the general formula

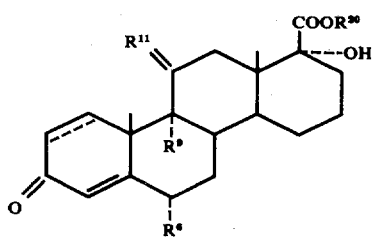

or l. functionally modifying the group $COOR^{20}$ in a D-homosteroid of the general formula

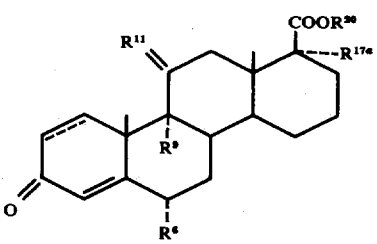

or m. degrading the 17aβ side-chain in a D-homosteroid of the general formula

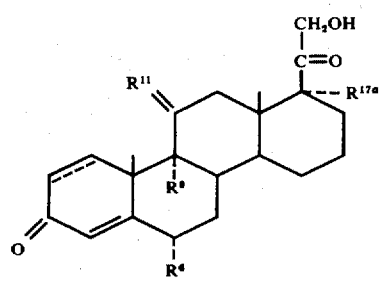

(XIII)

to the 17aβ-carboxyl group, or n. hydrogenating the 1,2-double bond in a D-homosteroid of the general formula

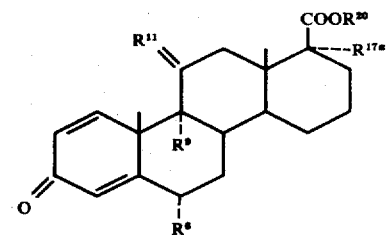

(XIV)

Wherein in the foregoing formulae $R^6$, $R^9$, $R^{11}$, $R^{17a}$ and $R^{20}$ and the broken line in the 1,2-position have the significance given earlier, $R^5$ is hydroxy, fluorine, chlorine or bromine, $R^{61}$ is hydrogen or methyl and $R^{62}$ is fluorine, chlorine or methyl.

The 1,2-dehydrogenation of a D-homosteroid of formula I in accordance with embodiment a) of the process can be carried out in a manner known per se; for example, in a microbiological manner or using a dehydrogenating agent such as iodine pentoxide, periodic acid, selenium dioxide, 2,3-dichloro-5,6-dicyanobenzoquinone, chloranil or lead tetraacetate. Suitable microorganisms for the 1,2-dehydrogenation are, for example, Schizomycetes, especially those of the genera Arthrobacter (e.g., A. simplex ATCC 6946), Bacillus (e.g., B. lentus ATCC 13805 and B. sphaericus ATCC 7055), Pseudomonas (e.g., P. aeruginosa IFO 3505), Flavobacterium (e.g., F. flavenscens IFO 3058), Lactobacillus (e.g., L. brevis IFO 3345) and Nocardia (e.g., N. opaca ATCC 4276).

The oxidation of a D-homosteroid of formula II in accordance with embodiment b) of the process can be carried out according to the Oppenauer procedure (e.g., using aluminum isopropylate) or by means of oxidation agents such as chromium trioxide (e.g., Jones' reagent) or according to the Pfitzner-Moffatt procedure using dimethylsulfoxide/dicyclohexylcarbodiimide (the initially obtained $\Delta^5$-3-ketone requiring subsequent isomerisation to the $\Delta^4$-3-ketone) or by means of pyridine/sulphur trioxide.

The fluorination or chlorination of a D-homosteroid of formula III in the 6-position in accordance with embodiment c) of the process can be carried out in a manner known per se. A 6,7-saturated D-homosteroid of formula III can be fluorinated or chlorinated by reaction with a fluorinating or chlorinating agent such as a N-chloroamide or imide (e.g. N-chlorosuccinimide) or with elemental chlorine [see J. Am. Chem. 72, 4534 (1950)]. This embodiment of the process is preferably carried out by converting a 6,7-saturated D-homosteroid of formula III into a 3-enol ester or 3-enol ether (e.g. the 3-enol acetate) and reacting the 3-enol ester or 3-enol ether with chlorine [see J. Am. Chem. Soc. 82, 1230 (1960)], with a N-chloroimide [see J. Am. Chem. Soc. 82, 1230 (1960); 77, 3827 (1955)] or with perchloryl fluoride [see J. Am. Chem. Soc. 81, 5259 (1959); Chem. and Ind. 1959, 1317]. Trifluoromethylhypofluorite can also be used as the fluorinating agent.

Insofar as the previously described fluorination or chlorination yields an isomeric mixture, that is to say, a mixture of 6α- and 6β-(fluoro or chloro)-D-homosteroids, the mixture can be separated into the pure isomers according to known methods such as chromatography.

The isomerisation of a 6β-(fluoro or chloro)-D-homosteroid to a 6α-(fluoro or chloro)-D-homosteroid can be carried out by treatment with an acid, especially a mineral acid such as hydrochloric acid or hydrobromic acid in a solvent (e.g. dioxane or glacial acetic acid).

The methylation of a D-homosteroid of formula IV in accordance with embodiment d) of the process can be carried out, for example, by converting a D-homosteroid of formula IV into a 3-enol ether (e.g. by treatment with an orthoformic acid ester such as ethyl orthoformate in the presence of an acid such as p-toluenesulphonic acid, if desired, with the addition of the corresponding alcohol; or by treatment with a dialkoxypropane such as 2,2-dimethoxypropane in methanol/dimethylformamide in the presence of p-toluenesulphonic acid) and reacting the enol ether with a tetrahalomethane (e.g. $CBr_4$, $CCl_2Br_2$ or $CCl_3Br$) to give a trihalomethyl-$\Delta^4$-3-ketone. A trihalomethyl-$\Delta^4$-3-ketone can be dehydrohalogenated with a base such as collidine to give a dihalomethylene-$\Delta^4$-3-ketone which can be converted into a 6α-methyl-$\Delta^4$-3-ketone by catalytic hydrogenation under mild conditions (e.g. using a Pd/$SrCO_3$ catalyst).

Another methylation procedure consists in converting a 1,2-saturated D-homosteroid of formula IV into a 3-enol ether as described earlier and reacting this 3-enol ether in a manner known per se to give a corresponding 6-formyl derivative, reducing the formyl group with sodium borohydride to the hydroxymethyl group and finally dehydrating the product obtained with cleavage of the enol ether, there being obtained a 6-methylene-D-homosteroid of the general formula

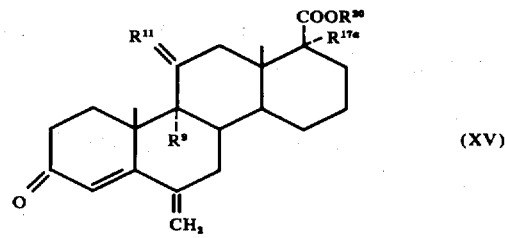

(XV)

, wherein $R^9$, $R^{11}$, $R^{17a}$ and $R^{20}$ have the significance given earlier.

6-Methylene-D-homosteroids of formula XV can also be prepared by converting a D-homosteroid of formula IV into a 3-enamine (e.g. the 3-pyrrolidinium enamine), hydroxymethylating the 3-enamine with formaldehyde and cleaving water from the hydroxymethylation product using an acid such as p-toluenesulphonic acid.

A 6-methylene-D-homosteroid of formula XV can be catalytically hydrogenated to give a corresponding 6-methyl-D-homosteroid of formula I in a manner known per se; for example, using a known hydrogenation catalyst.

The $HR^5$-cleavage from a D-homosteroid of formula V in accordance with embodiment e) of the process, namely a dehydration or a dehydrohalogenation, can be carried out in a manner known per se. The dehydration can be carried out by treatment with an acid (e.g. a mineral acid such as hydrochloric acid) or with a base. The dehydrohalogenation can be carried out using a base (e.g. an organic base such as pyridine).

In carrying out embodiments f) and g) of the process, a D-homosteroid of formula VI or VII is conveniently dissolved in a suitable solvent (e.g. an ether such as tetrahydrofuran or dioxane, a chlorinated hydrocarbon such as methylene chloride or chloroform or a ketone such as acetone) and left to react with the reagent added thereto. Hypochlorous or hypobromous acid is conveniently itself generated in the reaction mixture; for example, from N-bromo or N-chloroamides or imides such as N-chlorosuccinimide or N-bromoacetamide, and a strong acid, preferably perchloric acid. Embodiment g) is preferred for the manufacture of 9-fluoro-11-hydroxy-D-homosteroids of formula I.

The hydroxylation of a D-homosteroid of formula VIII in accordance with embodiment h) of the process can be carried out according to methods known per se for the microbiological 11-hydroxylation of steroids. For this 11-hydroxylation there can be used microorganisms of the taxonomic groups Fungi and Schizomycetes, especially of the sub-groups Ascomycetes, Phycomycetes, Basidiomycetes and Actinomycetales. There can also be used mutants produced in a chemical manner (e.g. by treatment with nitrite) or in a physical manner (e.g. by irradiation) as well as cell-free enzyme preparations obtained from the microorganisms. Especially suitable microorganisms for the 11$\beta$-hydroxylation are those of the genera Curvularia (e.g. C. lunata NRRL 2380 and NRRL 2178; ATCC 13633, 13432, 14678, IMI 77007, IFO 2811), Absidia (e.g. *A. coerula IFO* 4435), Colletotrichum (e.g. *C. pisi ATCC* 12520), Pellicolaria (e.g. *P. filamentosa IFO* 6675), Streptomyces (e.g. *S. fradiae* ATCC 10745), Cunninghamella (e.g. *C. bainieri* ATCC 9244, *C. Verticellata* ATCC 8983, *C. elegans* NRRL 1392 and ATCC 9245, *C. blakesleeana* ATCC 8688, 8688a, 8688b, 8983 and *C. echinulata* ATCC 8984), Pycnosporium (e.g. sp. ATCC 12231), Verticillium (e.g. *V. theobromae* CBS 39858), Aspergillus (e.g. *A. quadrilieatus* JAM 2763), Tricothecium (e.g. *T. roseum* ATCC 12519) an Phoma (e.g. sp. ATCC 13145).

In carrying out embodiment i) of the process, the keto group in the 3-position of a D-homosteroid of formula IX and the group —$COOR^{20}$ therein are firstly protected. The 3-keto group can be protected by ketalisation or, where a 1,2-double bond is present, also by formation of an enamine. A 20-carboxyl group can be protected by reaction with ethanolamine or 2,2-dimethylaziridine [Tetrah. Letters 30, 3031 (1972)] as the oxazoline. These protecting groups can subsequently be removed by acid hydrolysis. A $\Delta^{1,4}$-3-ketone can be converted into a $\Delta^{1,3,5}$-3-enamine using a secondary amine in the presence of titanium tetrachloride. The reduction of the 11-keto group of a thus-protected D-homosteroid can be carried out using a complex metal hydride such as lithium aluminum hydride, sodium borohydride or diisobutyl aluminum hydride.

The oxidation of the 11-hydroxy group in a D-homosteroid of formula X in accordance with embodiment j) of the process can be carried out using an oxidation agent such as chromic acid (e.g. $CrO_3$/sulphuric acid in acetone or $CrO_3$/pyridine).

The acylation of a 17a$\alpha$-hydroxy group in a D-homosteroid of formula XI in accordance with embodiment k) of the process can be carried out in a manner known per se; for example, by treatment with an acylating agent such as an acyl chloride or acid anhydride in the presence of an acid-binding agent (e.g. pyridine or triethylamine) or in the presence of a strong acid catalyst (e.g. p-toluenesulphonic acid). As the solvent for the acylation there may be mentioned organic solvents which do not contain hydroxyl groups (e.g. chlorinated hydrocarbons such as methylene chloride or hydrocarbons such as benzene). It is also possible to convert a 17a$\alpha$-hydroxy-D-homosteroid-17a$\beta$-carboxylic acid of formula XI with a corresponding carboxylic acid anhydride initially into a mixed anhydride of the steroid carboxylic acid and to treat this mixed anhydride with an acid or base (e.g. with aqueous acetic acid or aqueous pyridine) to give the desired 17a$\alpha$-acyloxy-D-homosteroid of formula I.

The functional modification of the group —$COOR^{20}$ in a D-homosteroid of formula XII in accordance with embodiment l) of the process can consist, for example, in an esterification of a 20-carboxyl group, a re-esterification of an esterified 20-carboxyl group or an esterification of a hydroxy group present in the group $R^{20}$. All of these reactions can be carried out according to methods known per se. The esterification can be carried out, for example, by treatment of the free acid with a diazoalkane (e.g. diazomethane in ether) or with an O-alkyl-N,N'-dicyclohexylisourea in an aprotic solvent or by reaction of a salt of the acid (e.g. an alkali salt) with an alkyl halide or sulphate (e.g. methyl or ethyl iodide or dimethyl or diethyl sulphate).

The acylation of a hydroxy group present in the group $R^{20}$ can be carried out in a manner analogous to that described earlier for the acylation of a 17a$\alpha$-hydroxy group. The re-esterification of an esterified carboxyl group (e.g. the replacement of an alkyl group denoted by $R^{20}$ by another alkyl group) can be carried out by reaction with the corresponding alcohol in the presence of an acid catalyst such as perchloric acid. D-Homosteroids in which $R^{20}$ represents a halo-(lower alkyl) or hydroxy-(lower alkyl) group can be manufactured, for example, by reacting a salt of a D-homosteroid carboxylic acid ester of formula XII with an appropriate sulphonyloxyalkyl halide and subjecting the resulting sulphonyloxyalkyl ester either to hydrolysis in order to obtain a hydroxy-(lower alkyl) substituent $R^{20}$ or to treatment with an alkali or alkaline earth halide (e.g. lithium chloride in dimethylformamide) in order to obtain a halo-(lower alkyl) substituent $R^{20}$. Halo-(lower alkyl) esters can also be obtained by reacting a D-homosteroid carboxylic acid with an appropriate aldehyde in the pesence of a hydrogen halide, conveniently in the presence of a catalyst such as zinc chloride.

The degradation of the 17a$\beta$ side-chain in a D-homosteroid of formula XIII in accordance with embodiment m) of the process can be carried out, for example, using periodic acid in a solvent such as methanol or using sodium bismuthate.

The hydrogenation of a 1,2-double bond in a D-homosteroid of formula XIV in accordance with embodiment n) of the process can be carried out catalytically; for example, using palladium or tris(triphenylphosphine)-rhodium chloride.

The starting materials used in the foregoing process, insofar as they are not known or insofar as their preparation is not described hereinafter, can be prepared in analogy to known methods or methods described in the Examples hereinafter.

The D-homosteroids of formula I possess endocrinal, especially antiinflammatory, activity. They show a good ratio of the antiinflammatory activity to effects of a mineralo or glucocorticoidal nature.

In the following Table there are compiled the results obtained with three D-homosteroids of formula I in standard tests which demonstrate the activity of this class of compound. The tests carried out can be described as follows:

1. Vasoconstriction test

This test demonstrates the antiinflammatory action on the experimentally hyperemiated skin [Brit. J. Derm. 69, 11 (1957)]. In this test, the degree of the vasoconstriction in relation to the time was estimated visually (after 4 and 8 hours). The colour value of the hyperemiated non-treated skin was rated as 0 and the colour value of the non-hyperemiated skin was rated as 100. The D-homosteroids were used in concentration of 0.1%.

2. Mouse ear test

The D-homosteroids, dissolved in croton oil, were applied for 15 seconds under a pressure of 600 g to the right ear of male mice weighing 25–30 g. The left ear served as the control. 4 hours later, the mice were killed and tissue was removed with a punch from the same position on treated and untreated ears and weighed. The $EC_{50}$, namely that concentration which gave a 50% oedema inhibition in comparison with a control group, was determined.

3. Felt pellet test 2 felt pellets were implanted under the skin (scapula region) in female rats (90–110 g) under ether narcosis. The D-homosteroids were administered orally on 4 successive days commencing on the day of the implantation. On the fifth day the rats were killed, the granulomas which formed were removed, dried and weighed. The $ED_{40}$, namely that dosage which gave a 40% reduction of the granulation weight, was determined. The thymus and kidney fresh weight as well as the weight-change were also determined.

4. Thymolysis test

Rats employed in the Felt pellet test were used for this test. The $ED_{50}$, namely that dosage which gave a 50% reduction in the thymus weight, was determined.

5. Adjuvant-paw oedema test

This test was carried out on female Lewis rats weighing 130–150 g. The oedema was caused by the subplantar injection of Mycobacterium butyricum in the right hind paw (0.5 mg of M. butyricum/0.1 ml of liquid paraffin). The D-homosteroids (suspended in 0.5% tragacanth/0.9% sodium chloride) were administered immediately before and 24 hours after the establishment of the oedema. The paw diameter was measured before and 48 hours after the establishment of the oedema. The $ED_{50}$, namely the dosage which brings about a 50% oedema inhibition, was determined by means of a graph.

Table

| D-Homo-steroid | (1) Vaso-constriction 4 hrs./ 8 hrs. | (2) Mouse ear $ED_{50}$ (mg/kg) | (3) Felt pellet $ED_{40}$ (mg/kg) | (4) Thymolysis $ED_{50}$ (mg/kg) | (5) Adjuvant oedema $ED_{50}$ (mg/kg) |
|---|---|---|---|---|---|
| 17aα-Acetoxy-9α-fluoro-11β-hydroxy-3-oxo-D-homoan-drosta-1,4-diene-17aβ-carboxylic acid methyl ester | 63/77 | 1 | 9 | 0.9 | 1.3 |
| 17aα-Acetoxy-11β-hydroxy-3-oxo-D-homo-androsta-1,4-diene-17aβ-carboxylic acid methyl ester | 70/77 | 0.5 | 3 | 0.65 | 3.5 |
| 17aα-Acetoxy-11β-hydroxy-3-oxo-D-homo-androst-4-ene-17aβ-carboxylic acid methyl ester | 72/70 | | | | |

The D-homosteroids of formula I can be used as medicaments in the form of pharmaceutical preparations having direct or delayed liberation of the active ingredient which contain them in association with a compatible pharmaceutical carrier material. This carrier material can be an organic or inorganic inert carrier material suitable for enteral, percutaneous or parenteral application such as water, gelatine, gum arabic, lactose, starch, magnesium stearate, talc, vegetable oils, polyalkyleneglycols, petroleum jelly etc. The pharmaceutical preparations can be made up in a solid form (e.g. tablets, dragees, suppositories or capsules), in a semi-solid form (e.g. as salves) or in a liquid form (e.g. as solutions, suspensions or emulsions). If necessary, the pharmaceutical preparations can be sterilised and/or can contain adjuvant substances such as preserving, stabilising, wetting or emulsifying agents, salts for the variation of the osmotic pressure or substances acting as buffers.

In general, the dosage range in the case of pharmaceutical preparations for topical administration can be about 0.01–1% of a D-homosteroid of formula I. In the case of pharmaceutical preparations for systemic administration, about 0.1–10 mg of a D-homosteroid of formula I can be provided per administration.

The pharmaceutical preparations can be prepared in a manner known per se by mixing a D-homosteroid of formula I with non-toxic solid and/or liquid carrier materials which are customary in pharmaceutical preparations and which are suitable for therapeutic administration (e.g. those carrier materials mentioned earlier) and, if desired, transforming the mixture into the desired pharmaceutical dosage form.

The following examples illustrate the invention.

EXAMPLE 1

950 mg of D-homocortisone in 47 ml of methanol were treated with 1.42 g of periodic acid in 9.5 ml of water and the mixture was stirred under argon for 4 hours at room temperature. The mixture was concentrated under reduced pressure until a precipitate formed. Precipitation was completed with ca 200 ml of water, and the precipitate was filtered off under suction and dried. There was obtained 11β,17aα-dihydroxy-3-oxo-D-homoandrost-4-ene-17aβ-carboxylic acid of melting point 274°–275° C (from alcohol/ether); UV: $\epsilon_{242} = 15,300$; $[\alpha]_D = +92°$ (c =0.103% in dioxane).

In an analogous manner,
from 9α-fluoro-11β,17aα,21-trihydroxy-D-homopregna-1,4-diene-3,20-dione there was obtained 9α-fluoro-11,β,17aα-dihydroxy-3-oxo-D-homoandrosta-1,4-diene-17aβ-carboxylic acid of melting point 273°–274° C; UV: $\epsilon_{239} = 14,900$; $[\alpha]_D = +32°$ (c = 0.1% in dioxane);

from 11β,17aα,21-trihydroxy-D-homopregna-1,4-diene-3,20-dione there was obtained 11β,17aα-dihydroxy-3-oxo-D-homo-androsta-1,4-diene-17aβ-carboxylic acid of melting point 237°–238° C; UV: $\epsilon_{243} = 14,600$; and from 6α-fluoro-11β,17aα,21-trihydroxy-D-homopregna-1,4-diene-3,20-dione there was obtained 6α-fluoro-11β,17aα-dihydroxy-3-oxo-D-homoandrosta-1,4-diene-17aβ-carboxylic acid; UV: $\epsilon_{243} = 14,900$.

EXAMPLE 2

A solution of 120 mg of 11β,17aα-dihydroxy-3-oxo-D-homoandrost-4-ene-17aβ-carboxylic acid and 0.13 ml of triethylamine in 3.1 ml of methylene chloride was treated dropwise at 0° C with 0.88 ml of acetyl chloride and the mixture was stirred for 40 minutes. The mixture was diluted with methylene chloride and washed successively with 3% sodium hydrogen carbonate solution, 1-N hydrochloric acid and water, dried and evaporated. The residue was dissolved in 3.1 ml of acetone and treated with 0.1 ml of diethylamine. The mixture was concentrated in vacuo, the precipitate which thereby separated was filtered off under suction, dissolved in water, acidified with 2-N hydrochloric acid and extracted with ethyl acetate. After drying and evaporation of the solvent, there was obtained 17aα-acetoxy-11β-hydroxy-3-oxo-D-homoandrost-4-ene-17aβ-carboxylic acid of melting point 167°–170° C (from acetone/hexane); UV: $\epsilon_{241} = 13,900$; $[\alpha]_D = 39°$ (c =0.1% in dioxane).

In an analogous manner,
from 11β,17aα-dihydroxy-3-oxo-D-homoandrost-4-ene-17aβ-carboxylic acid methyl ester there was obtained 17aα-acetoxy-11β-hydroxy-3-oxo-D-homoandrost-4-ene-17aβ-carboxylic acid methyl ester of melting point 235°–237° C (from ether); UV: $\epsilon_{242} = 15,750$; $[\alpha]_D = +49°$ (c = 0.1% in dioxane);

from 9°-fluoro-11β,17aβ-dihydroxy-3-oxo-D-homoandrosta-1,4-diene-17aβ-carboxylic acid there was obtained 17aα-acetoxy-9α-fluoro-11β-hydroxy-3-oxo-D-homoandrosta-1,4-diene-17aβ-carboxylic acid of melting point 232°–234° C; UV: $\epsilon_{240} = 15,200$; $[\alpha]_D = +6°$ (c = 0.108% in dioxane);

from 11β,17aβ-dihydroxy-3-oxo-D-homoandrosta-1,4-diene-17aβ-carboxylic acid there was obtained 17aα-acetoxy-11β-hydroxy-3-oxo-D-homoandrosta-1,4-diene-17aβ-carboxylic acid of melting point 251° C (decomposition); UV: $\epsilon_{243} = 14,500$; $[\alpha]_D = +25°$ (c =0.1% in methanol); and from 6α-fluoro-11β,17aα-dihydroxy-3-oxo-D-homoandrosta-1,4-diene-17aβ-carboxylic acid there was obtained 17aα-acetoxy-6α-fluoro-11β-hydroxy-3-oxo-D-homoandrosta-1,4-diene-17aβ-carboxylic acid of melting point 208° C (from acetone/hexane); UV: $\epsilon_{243} = 14,650$; $[\alpha]_D = +21°$ (c = 0.1% in methanol).

EXAMPLE 3

50 mg of 11β,17aα-dihydroxy-3-oxo-D-homoandrost-4-ene-17aβ-carboxylic acid were dissolved in 3 ml of methanol and treated at 0° C with 2.6 ml of a 0.06-N ethereal diazomethane solution. After 5 minutes, several drops of acetic acid were added and the mixture was evaporated. Filtration on 1 g of aluminium oxide gave 11β,17aβ-dihydroxy-3-oxo-D-homoandrost-4-ene-17aβ-carboxylic acid methyl ester of melting point 186°–188° C (from ether); UV: $\epsilon_{243} = 15,750$; $[\alpha]_D = +95°$ (c = 0.1% in dioxane).

In an analogous manner,
from 17aα-acetoxy-11β-hydroxy-3-oxo-D-homoandrost-4-ene-17aβ-carboxylic acid there was obtained 17aα-acetoxy-11β-hydroxy-3-oxo-D-homoandrost-4-ene-17aβ-carboxylic acid methyl ester of melting point 235°–237° C (from ether); UV: 15,750; $[\alpha]_D = +49°$ (c = 0.1% in dioxane);

from 17aα-acetoxy-9-fluoro-11β-hydroxy-3-oxo-D-homo-androsta-1,4-diene-17aβ-carboxylic acid there was obtained 17aα-acetoxy-9-fluoro-11β-hydroxy-3-oxo-D-homoandrosta-1,4-diene-17aβ-carboxylic acid methyl ester of melting point 244°–245° C; UV: $\epsilon_{240}$ =15,100; $[\alpha]_D = +14°$ (c = 0.1% in dioxane);

from 17aα-acetoxy-11β-hydroxy-3-oxo-D-homoandrosta-1,4-diene-17aβ-carboxylic acid there was obtained 17aα-acetoxy-11β-hydroxy-3-oxo-D-homoandrosta-1,4-diene-17aβ-carboxylic acid methyl ester of melting point 235°–237° C; UV: $\epsilon_{242} = 15,100$; $[\alpha]_D = +13°$ (c = 0.1% in dioxane);

from 17aα-acetoxy-6aα-acetoxy-6α-fluoro-11β-hydroxy-3-oxo-D-homoandrosta-1,4-diene-17aβ-carboxylic acid there is obtained 17aα-acetoxy-6α-fluoro-11β-hydroxy-3-oxo-D-homoandrosta-1,4-diene-17aβ-carboxylic acid methyl ester of melting point 238°–239° C; UV: $\epsilon_{242} = 15,550$; $[\alpha]_d = +31°$ (c = 0.1% in methanol); and from 11β-hydroxy-3-oxo-17aα-propionyloxy-D-homoandrost-4-ene-17aβ-carboxylic acid there is obtained 11β-hydroxy-3-oxo-17aα-propionyloxy-D-homoandrost-4-ene-17aβ-carboxylic acid methyl ester; UV: $\epsilon_{241} = 14,900$; $[\alpha]_D = +48°$ ($c = 0.102\%$ in dioxane).

EXAMPLE 4

A solution of 3.2 g of 11β,17aα-dihydroxy-3-oxo-D-homoandrost-4-ene-17aβ-carboxylic acid and 4.2 ml of triethylamine in 86 ml of methylene chloride were treated dropwise at 0° C under argon with 29 ml of propionyl chloride and the mixture was stirred for 45 minutes. The mixture was poured into ice-cold dilute hydrochloric acid and extracted three times with methylene chloride. The organic solution was washed with sodium chloride solution, dried and evaporated. Still present residues of propionic acid were removed by repeated evaporation with toluene. The 11β-hydroxy-3-oxo-17aα-propionyloxy-D-homoandrost-4-ene-17aβ-carboxylic acid was obtained as a non-crystalline foam; UV: $\epsilon_{241} = 15,000$; $[\alpha]_D = +37°$ ($c = 0.1\%$ in dioxane).

In the same manner, from 9α-fluoro-11β,17aα-dihydroxy-3-oxo-D-homoandrosta-1,4-diene-17aβ-carboxylic acid there was obtained 9α-fluoro-11β-hydroxy-3-oxo-17aα-propionyloxy-D-homoandrosta-1,4-diene-17aβ-carboxylic acid of melting point 221° C; UV: $\epsilon_{240} = 14,500$; $[\alpha]_D = +11°$ ($c = 0.1\%$ in dioxane).

EXAMPLE 5

420 mg of 11β-hydroxy-3-oxo-17aα-propionyloxy-D-homoandrost-4-ene-17aβ-carboxylic acid, 0.5 ml of triethylamine and 0.5 ml of n-butyl iodide were boiled under reflux for 48 hours in 10 ml of acetone. The mixture was poured into ice-cold dilute hydrochloric acid and extracted with methylene chloride. The organic solution was washed with sodium chloride solution, dried and evaporated, there being obtained 11β-hydroxy-3-oxo-17aα-propionyloxy-D-homoandrost-4-ene-17aβ-carboxylic acid butyl ester of melting point 150°–151° C (from acetone/hexane); UV: $\epsilon_{241} = 16,150$; $[\alpha]_D = +41°$ ($c = 0.104\%$ in dioxane).

In an analogous manner, from 17aα-acetoxy-11β-hydroxy-3-oxo-D-homoandrosta-1,4-diene-17aα-acetoxy-11β-hydroxy-3-oxo-D-homoandrosta-1,4-diene-17aα-acetoxy-11β-hydroxy-3-oxo-D-homoandrosta-1,4-diene-17aβ-carboxylic acid methyl ester which was identical with the D-homosteroid obtained in Example 3.

EXAMPLE 6

250 mg of 11β-hydroxy-3-oxo-17aα-propionyloxy-D-homoandrost-4-ene-17aβ-carboxylic acid butyl ester were dissolved in 130 ml of water and covered with 25 ml of water. 2.5 ml of Jones' reagent were added thereto and the mixture was stirred for an additional 10 minutes. The mixture was poured into dilute sodium bicarbonate solution and extracted with ether. The ether solutions were washed with water, dried and evaporated. After filtration on silica gel, there was obtained 3,11-dioxo-17aα-propionyloxy-D-homoandrost-4-ene-17aβ-carboxylic acid butyl ester of melting point 154°14 156° C (from acetone/hexane); UV: $\epsilon_{238} = 16,250$; $[\alpha]_d = +77°$ ($c = 0.103\%$ in dioxane).

EXAMPLE 7

500 mg of 17aα-acetoxy-3-oxo-D-homoandrosta-4,9(11)-diene-17aα-carboxylic acid methyl ester in 6.5 ml of chloroform were treated at 0° C with 1.26 ml of carbon tetrachloride saturated with chlorine and the mixture was stirred under argon. After 2 hours, a further 0.6 ml of chloroform was added and the mixture stirred for 30 minutes. The mixture was evaporated and the residue chromatographed on silica gel with hexane/acetone, there being obtained 17aα-acetoxy-9α,11β-dichloro-3-oxo-D-homoandrost-4-ene-17aβ-carboxylic acid methyl ester of melting point 241° C; UV: $\epsilon_{240} = 17,100$; $[\alpha]_D = +89°$ ($c = 0.102\%$ in methanol).

The starting material was prepared as follows:

780 mg of 17aαacetoxy-11β-hydroxy-3-oxo-D-homoandrost-4-ene-17aβ-carboxylic acid methyl ester in 7.5 ml of dimethylformamide and 3.7 ml of pyridine were treated at 0° C with 0.84 ml of a 5% sulphur dioxide solution in dimethylformamide and subsequently dropwise with 0.17 ml of methanesulphonyl chloride. After stirring for 2 hours at room temperature, 6 ml of water were added and the mixture was stirred for a further 10 minutes. The mixture was then poured into dilute sodium chloride solution, extracted three times with methylene chloride, washed twice with dilute sodium chloride solution, dried and evaporated. Still present dimethylformamide was removed by repeated evaporation with toluene. Chromatography on silica gel gave 17aα-acetoxy-3-oxo-D-homoandrosta-4,9(11)-diene-17aβ-carboxylic acid methyl ester of melting point 196°–203° C; UV: $\epsilon_{239} = 16,800$.

EXAMPLE 8

900 mg of 11β-hydroxy-17aα-propionyloxy-3-oxo-D-homoandrost-4-ene-17aβcarboxylic acid in 3 ml of dimethylformamide were treated with 0.5 ml of triethylamine and 1 ml of chloroiodomethane and the mixture was stirred at room temperature. After 24 and 48 hours, 0.5 ml of triethylamine and 1 ml of chloroiodomethane were again added. After a total of 72 hours, the mixture was poured into ice-cold dilute hydrochloric acid, extracted with methylene chloride, washed with dilute sodium chloride solution, dried and evaporated. After chromatography on silica gel, there was obtained 11β-hydroxy-17aα-propionyloxy-3-oxo-D-homoandrost-4-ene-17aβ-carboxylic acid chloromethyl ester of melting point 180°–181° C; UV: $\epsilon_{242} = 17,350$; $[\alpha]_D = +\mu°$ ($c = 0.1045$ in dioxane).

EXAMPLE 9

500 mg of 11β-hydroxy-17aα-propionyloxy-3-oxo-D-homoandrost-4-ene-17aβ-carboxylic acid chloromethyl ester in 65 ml of acetonitrile were treated with 1 g of silver fluoride and the mixture was stirred. After 3 days, 0.5 g of silver fluoride was again added. After a further 3 days, the mixture was diluted with ethyl acetate and filtered through silica gel. The eluate was washed with water, dried and evaporated. Chromatography on silica gel gave 11β-hydroxy-17aα-propionyloxy-3-oxo-D-homoandrost-4-ene-17aβ-carboxylic acid fluoromethyl ester of melting point 171° C; UV: $\epsilon_{240} = 23,700$; $[\alpha]_D = +59°$ ($c = 0.101\%$ in dioxane).

EXAMPLE 10

360 mg of 17aα-acetoxy-11β-hydroxy-3-oxo-D-homoandrost-4-ene-17aβ-carboxylic acid methyl ester and 250 mg of selenium dioxide were boiled under reflux under argon for 20 hours in 20 ml of tert.butanol and 0.2 ml of glacial acetic acid. The mixture was filtered and evaporated. The oil obtained was dissolved in ethyl acetate and washed successively with sodium hydrogen carbonate solution, water, ice-cold ammonium sulphide solution, dilute ammonia, water, dilute hydrochloric acid and water. The ethyl acetate solution was dried over sodium sulphate and evaporated. Chromatography on silica gel gave 17aα-acetoxy-11β-hydroxy-3-oxo-D-homoandrosta-1,4-diene-17aβ-carboxylic acid methyl ester of melting point 235°–237° C which was identical with the D-homosteroid obtained according to Example 3.

EXAMPLE 11

A nutrient medium consisting of 0.15% cornsteep, 0.5% peptone and 0.5% glucose in distilled water, pH 7.3, was inoculated with Arthrobacter simplex ATCC 6946. The culture was left to grow for 24 hours at 28° C and then a solution of 25 mg of 11β,17aα-dihydroxy-3-oxo-D-homoandrost-4-ene-17aβ-carboxylic acid in 1 ml of aqueous methanol was added. After an incubation duration of 48–72 hours, the mycelium is separated from the substrate and washed with water. The wash-water combined with the substrate is extracted with methylene chloride. Working-up of the extract yields 11β, 17aα-dihydroxy-3-oxo-D-homoandrosta-1,4-diene-17aβ-carboxylic acid which is identical with the D-homosteroid obtained according to Example 1.

EXAMPLE 12

505 mg of 17aα-acetoxy-3-oxo-D-homoandrosta-1,4,9(11)-triene-17aβ-carboxylic acid methyl ester (melting point 228°-229° C, prepared from 17aα-acetoxy-11β-hydroxy-3-oxo-D-homoandrasta-1,4-diene-17aβ-carboxylic acid methyl ester in accordance with the second paragraph of Example 7) and 445 mg of N-chlorosuccinimide were treated with 5.1 ml of urea-HF solution (1 mol urea: 4 mol HF) and the mixture was stirred at room temperature for 30 minutes. The mixture was poured into water and extracted with methylene chloride. The methylene chloride extracts were washed with dilute sodium bicarbonate solution and sodium chloride solution, dried and evaporated. The crude product was chromatographed on silica gel with ether/hexane. After crystallisation from acetone/hexane, there was obtained pure 17aβ-acetoxy-9-chloro-11β-fluoro-3-oxo-D-homoandrosta-1,4-diene-17aβ-carboxylic acid methyl ester of melting point 215°–216° C; UV: $\epsilon_{236}$ = 15,400, $[a]_D$ = +46° (dioxane, c = 0.1%).

EXAMPLE 13

2.5 g of 17aα-acetoxy-3-oxo-D-homoandrosta-1,4,9(11)-triene-17aβ-carboxylic acid methyl ester in 100 ml of dioxane and 10 ml of water were treated with 1.73 g of N-bromoacetamide and 11.1 ml of 10% perchloric acid and the mixture was stirred at room temperature for 10 minutes. 9 g of sodium sulphite in 900 ml of water were then added. After stirring for a short time, the mixture was extracted with methylene chloride, washed with water, dried and evaporated. The crude 17aα-acetoxy-9-bromo-11β-hydroxy-3-oxo-D-homoandrosta-1,4-diene-17aβ-carboxylic acid methyl ester and 1.5 g of dry potassium acetate were boiled under reflux in 150 ml of alcohol for 24 hours. The mixture was concentrated, poured into water and extracted with methylene chloride. The organic extract was washed, dried and evaporated. The resulting crude 17aα-acetoxy-9β,11β-epoxy-3-oxo-D-homoandrosta-1,4-diene-17aβ-carboxylic acid methyl ester was stirred at room temperature for 20 minutes in 30 ml of a solution of 1.25 parts of hydrogen fluoride in 1 part of urea. The mixture was poured into ice-water and extracted with methylene chloride. The organic extract was washed with dilute sodium chloride solution, dried and evaporated. Chromatography on silica gel gave 17aα-acetoxy-9-fluoro-11β-hydroxy-3-oxo-D-homoandrosta-1,4-diene-17aβ-carboxylic acid methyl ester which was identical with the D-homosteroid obtained according to Example 3.

EXAMPLE 14

1.05 g of 11β-hydroxy-3-oxo-17aα-propionyloxy-D-homoandrost-4-ene-17aβ-carboxylic acid methyl ester in 10 ml of orthoformic acid methyl ester and 10 ml of methanol were treated with 10 ml of p-toluenesulphonic acid in a small amount of methanol and the mixture was stirred at room temperature for 10 minutes. After the addition of 2 drops of pyridine, the mixture was poured into dilute sodium hydrogen carbonate solution and extracted with methylene chloride. The methylene chloride extracts were washed with dilute sodium chloride solution, dried and evaporated. The crude 11β-hydroxy-3-oxo-17aα-propionyloxy-D-homoandrosta-3,5-diene-17aβ-carboxylic acid methyl ester in 35 ml of dimethylformamide and 3.5 Lml of water was gassed with perchloryl fluoride at 0° C for 20 minutes. The mixture was poured into water and extracted with methylene chloride. The extracts were washed with dilute sodium chloride solution, dried and evaporated. The residue was dissolved in 40 ml of glacial acetic acid, treated with 0.4 ml of 30% hydrogen bromide in glacial acetic acid and left to stand at room temperature for 1 hour. The mixture was then poured into ice-water, extracted with methylene chloride, washed neutral with dilute sodium hydrogen carbonate solution and dilute sodium chloride solution, dried and evaporated. Chromatography on silica gel yielded 6α-fluoro-11β-hydroxy-3-oxo-17aα-propionyloxy-D-homoandrost-4-ene-17acarboxylic acid methyl ester; UV: $\epsilon_{234}$ = 15,900.

EXAMPLE 15

500 mg of 3,11-dioxo-17aα-propionyloxy-D-homoandrost-4-ene-17aβ-carboxylic acid methyl ester and 50 mg of p-toluene-sulphonic acid in 70 ml of benzene and 5 ml of ethyleneglycol were boiled under a water-separator for 5 hours. After cooling, the benzene solution was washed with dilute sodium bicarbonate solution and dilute sodium chloride solution, dried and evaporated. The crude 3,3-ethylenedioxy-11-oxo-17aα-propionyloxy-D-homoandrost-5-ene-17aβ-carboxylic acid methyl ester was dissolved in 25 ml of tetrahydrofuran and 12.5 ml of methanol, treated with 600 mg of sodium borohydride in 3 ml of water and stirred at 20° C for 8 hours. The mixture was poured into water and extracted three times with methylene chloride. The methylene chloride extracts were washed with dilute sodium chloride solution, dried and evaporated. The crude 3,3-ethylenedioxy-11β-hydroxy-17aα-propionyloxy-D-homoandrost-5-ene-17aβ-carboxylic acid methyl ester and 50 mg of p-toluenesulphonic acid in 15 ml of acetone were stirred at 20° C for 16 hours.

The mixture was poured into dilute sodium bicarbonate solution and extracted with methylene chloride. The methylene chloride extracts were washed with dilute sodium chloride solution, dried and evaporated. Chromatography of the residue obtained on silica gel yielded 11β-hydroxy-3-oxo-17aα-propionyloxy-D-homoandrost--4-ene-17aβ-carboxylic acid methyl ester of melting point 150°-151° C (from acetone/hexane); UV: $\epsilon_{241}$ = 16,150; $[a]_D$ = +41°(c = 0.1% in dioxane).

EXAMPLE 16

200 ml of 17aα-acetoxy-11β-hydroxy-3-oxo-D-homoandrosta---1,4-diene-17aβ-carboxylic acid methyl ester and 200 mg of tris(triphenylphosphine)-rhodium (I) chloride were dissolved under hydrogen in 4 ml of benzene and 4 ml of alcohol and the mixture was hydrogenated at 20° C overnight. Chromatography on silica gel yielded 17aβ-acetoxy-11β-hydroxy-3-oxo-D-homoandrost-4-ene-17a-β-carboxylic acid methyl ester of melting point 235°-237° C (from ether); UV: $\epsilon_{242}$ = 15,750; $[a]_D$ = +49° (c = 0.1% in dioxane).

EXAMPLE 17

230 mg of 17aα-acetoxy-11β-hydroxy-6-methylene-3-oxo-D--homoandrost-4-ene-17aβ-carboxylic acid methyl ester and 80 mg of 1,4-diazobicyclo[2.2.2]octane were dissolved in 17 ml of methoxyethanol, treated with 30 mg of 5% palladium/carbon and shaken under hydrogen until hydrogen was no longer taken up. The catalyst was filtered off under argon and the filtrate treated with 1.3 ml of 25% hydrochloric acid. After 1 hour, the mixture was poured into water, extracted with methylene chloride, washed neutral with sodium hydrogen carbonate solution and sodium chloride solution, dried and evaporated. Chromatography on silica gel yielded 17aα-acetoxy-11β-hydroxy-6α-methyl-3-oxo-D-homoandrost-4-ene-17aβ-carboxylic acid methyl ester; UV: $\epsilon_{242}$ = 15,000.

The starting material was prepared as follows:

2.0 g of 17aα-acetoxy-11β-hydroxy-3-oxo-D-homoandrost-4-ene-17aα-carboxylic acid methyl ester were dissolved in 20 ml of methanol and, after the addition of 1.5 ml of pyrrolidine, the mixture was heated to reflux under nitrogen for 10 minutes. The solution obtained was maintained at −10° C overnight. The crystalline precipitate was filtered off and dried at room temperature under reduced pressure. There were obtained 2.0 g of 17aα-acetoxy-11β-hydroxy-3-pyrrolidino-D-homoandrosta-3,5-diene-17aβ-carboxylic acid methyl ester; UV: $\epsilon_{278}$ = 19,500.

2.0 g of 17aα-acetoxy-11β-hydroxy-3-pyrrolidino-D-homoandrosta-3,5-diene-17aβ-carboxylic acid methyl ester were stirred at room temperature for 45 minutes with a mixture of 11 ml of benzene, 50 ml of methanol and 4 ml of 35% formaldehyde solution. The crude product obtained by the usual working-up was chromatographed on silica gel with methylene chloride/acetone (9:1) and yielded 1.1 g of pure 17aα-acetoxy-11β-hydroxy-6β-hydroxymethyl-3-oxo-D-homoandrost-4-ene-17aβ-carboxylic acid methyl ester. 1.0 g of this D-homosteroid was dissolved in 50 ml of dioxane and stirred at room temperature for 2 hours with 1 ml of water and 1 ml of concentrated hydrochloric acid. After the usual working-up and chromatography of the crude product, there was obtained pure 17aα-acetoxy-11β-hydroxy-6-methylene-3-oxo-D-homoandrost-4-ene-17aβ-carboxylic acid methyl ester; UV: $\epsilon_{261}$ = 11,200.

EXAMPLE 18

A solution of 1.0 g of 17aα-acetoxy-3β,11β-dihydroxy-D-homoandrost-5-ene-17aβ-caarboxylic acid methyl ester in 50 ml of acetone was cooled to 0° C and treated within 5 minutes while cooling and stirring with 1.8 ml of Jones' reagent. The mixture was stirred for a further 10 minutes at 0° C, then treated with 1 ml of isopropanol, stirred at 0° C for a further 15 minutes, treated with 5 ml of 4-N hydrochloric acid, again stirred for 30 minutes and then worked-up as usual. The crude product was chromatographed on silica gel and yielded 0.5 g of pure 17aα-acetoxy-3,11-dioxo-D-homoandrost-4-ene -17aβ-carboxylic acid methyl ester; UV: $\epsilon_{240}$ = 16,000.

The following Examples illustrate typical pharmaceutical preparations (salves) containing the D-homosteroids of formula I hereinbefore as the active ingredient:

EXAMPLE A

| Active ingredient | 0.1 wt. % |
|---|---|
| Liquid paraffin | 10.0 wt. % |
| White soft paraffin q.s. ad | 100 parts by weight |

The active ingredient (D-homosteroid) is ground with some of the liquid paraffin in a ball mill until a particle size of less than 5 μ is attained. The paste is diluted and the ball mill is washed out with the remainder of the liquid paraffin. The suspension is added to the melted colourless white paraffin at 50° C and the mixture is stirred until it becomes cold, there being obtained a homogeneous salve.

EXAMPLE B

| Active ingredient | 0.25 wt. % |
|---|---|
| Aluminium stearate | 3.2 wt. % |
| Liquid paraffin g.s. ad | 100 parts by weight |

The aluminum stearate is dispersed in liquid paraffin by vortex-stirring. The suspension is heated with further stirring, the temperature increase being carried out at a rate of 2° C per minute until a temperature of 90° C is attained. The temperature is held at 90° C to 95° C for 30 minutes until a gel is formed. It is then cooled down rapidly. The active ingredient (D-homosteroid) is milled to a particle size of below 5 μ, ground thoroughly with a small portion of the gel and finally worked into the remaining portion of the gel, there being thus obtained a homogeneous mixture.

EXAMPLE 19

In analogy to the method described in Example 1 there was obtained 6α,9-difluoro-11β,17aα-dihydroxy-3-oxo-D-homoandrosta-1,4-diene-17aβ-carboxylic acid, UV: $\epsilon_{238}$ = 16450, from 6α,9-Difluoro-11β,17aα,21-trihydroxy-D-homopregna-1,4-diene-3,20-dione.

Example 20

In analogy to the method described in Example 2 there was obtained 17aα-acetoxy-6α,9-difluoro-11β- hydroxy-3-oxo-D-homoandrosta-1,4-diene-17aβ-carboxylic acid, UV: $\epsilon_{238}$ = 16300, from 6α,9-difluoro-11β,17aα-dihydroxy-3-oxo-D-homoandrosta-1,4-diene-17aβ-carboxylic acid.

EXAMPLE 21

In analogy to the method described in Example 3 there was obtained 17aα-acetoxy-6α,(9-difluoro-11β-hydroxy-3-oxo-D-homoandrosta-1,4-diene-17aβ-carboxylic acid methyl ester of melting point 291°-292° C; UV: $\epsilon_{238}$ = 16600; $[\alpha]_D$ = +13° (c = 0.1% in dioxane); from 17aα-acetoxy-6α,9-difluoro-11β-hydroxy-3-oxo-D-homoandrosta-1,4-diene-17aβ-carboxylic acid.

We claim:

1. A D-homosteroid of the formula

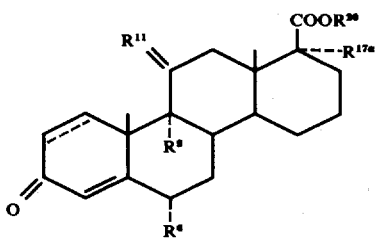

wherein $R^6$ is hydrogen, fluorine, chlorine or methyl; $R^9$ is hydrogen, fluorine, chlorine or bromine; $R^{11}$ is oxo or (α-H, β-OH) when $R^9$ is hydrogen, oxo, (α-H, β-OH), (α-H, β-fluoro) or (α-H,β-chloro) when $R^9$ is fluorine, chlorine or bromine with the proviso that, in the case of 9,11-dihalo compounds, the atomic number of the halogen atom in the 9-position is not less than the atomic number of the halogen atom in 11-position; $R^{17a}$ is hydroxy or acyloxy and $R^{30}$ is hydrogen, lower alkyl, halo-(lower alkyl), hydroxy-(lower alkyl), acyloxy-(lower alkyl) or (lower alkoxycarbonyl)-(lower alkyl) and wherein the broken line in the 1,2-position denotes an optional carbon-carbon bond said acyloxy groups being derived from a saturated or unsaturated aliphatic or cycloaliphatic carboxylic acid containing up to 15 carbon atoms or phenyl acetic acid or benzoic acid.

2. A compound of claim 1, wherein $R^{11}$ is (α-H, β-OH).

3. A compound of claim 2 which is 11β,17aα-dihydroxy-3-oxo-D-homoandrost-4-ene-17aβ-carboxylic acid.

4. A compound of claim 2 which is 11β,17aα-dihydroxy-3-oxo-D-homoandrosta-1,4-diene-17-aβ-carboxylic acid.

5. The compound of claim 2 which is 9α-fluoro-11β,17aα-dihydroxy-3-oxo-D-homoandrost-4-ene-17aβ-carboxylic acid.

6. The compound of claim 2 which is 9α-fluoro-11β,17aα-dihydroxy-3-oxo-D-homoandrosta-1,4-diene-17aβ-carboxylic acid.

7. The compound of claim 2 which is 6α,9β-difluoro-11β,17aα-dihydroxy-3-oxo-D-homoandrost-4-ene-17aβ-carboxylic acid.

8. The compound of claim 2 which is 6α,9α-difluoro-11β,17aα-dihydroxy-3-oxo-D-homoandrosta-1,4-diene-17aβ-carboxylic acid.

9. The compound of claim 2 which is 6α-chloro-11β,17aα-dihydroxy-3-oxo-D-homoandrost-4-ene-17aβ-carboxylic acid.

10. The compound of claim 2 which is 6α-chloro-9α-fluoro-11β,17aα-dihydroxy-3-oxo-D-homoandrost-4-ene-17aβ-carboxylic acid.

11. The compound of claim 2 which is 6α-chloro-9α-fluoro-11β,17aα-dihydroxy-3-oxo-D-homoandrost-1,4-diene-17aβ-carboxylic acid.

12. The compound of claim 2 which is 11β,17aα-dihydroxy-6α-methyl-3-oxo-D-homoandrost-4-ene-17aβ-carboxylic acid.

13. The compound of claim 2 which is 6α-fluoro-11β,17aα-dihydroxy-3-oxo-D-homoandrosta-1,4-diene-17aβ-carboxylic acid.

14. The compound of claim 2 which is 17aα-acetoxy-11β-hydroxy-3-oxo-D-homoandrost-4-ene-17aβ-carboxylic acid.

15. The compound of claim 2 which is 17aα-acetoxy-11β-hydroxy-3-oxo-D-homoandrosta-1,4-diene-17aβ-carboxylic acid.

16. The compound of claim 2 which is 17aα-acetoxy-11β-hydroxy-3-oxo-D-homoandrost-4-ene-17aβ-carboxylic acid methyl ester.

17. The compound of claim 2 which is 17a9α-fluoro-11β-hydroxy-3-oxo-D-homoandrosta-1,4-diene-17aβ-carboxylic acid.

18. The compound of claim 2 which is 17aα-acetoxy-6α-fluoro-11β-hydroxy-3-oxo-D-homoandrosta-1,4-diene-17aβ-carboxylic acid.

19. The compound of claim 2 which is 17aα-acetoxy-6α-fluoro-11β-hydroxy-3-oxo-D-homoandrosta-1,4-diene-17aβ-carboxylic acid methyl ester.

20. The compound of claim 2 which is 11β,17aα-dihydroxy-3-:oxo-D-homoandrost-4-ene-17aβ-carboxylic acid methyl ester.

21. The compound of claim 2 which is 17aα-acetoxy-11 α-hydroxy-3-oxo-D-homoandrosta-1,4-diene-17aβ-carboxylic acid methyl ester.

22. The compound of claim 2 which is 11β-hydroxy-3-oxo-17aα-propionyloxy-D-homoandrost-4-ene-17aβ-carboxylic acid.

23. The compound of claim 2 which is 11β-hydroxy-3-oxo-17aα-propionyloxy-D-homoandrost-4-ene-17aβ-carboxylic acid methyl ester.

24. The compound of claim 2 which is 11β-hydroxy-3-oxo-17aα-propionyloxy-D-homoandrost-4-ene-17aβ-carboxylic acid butyl ester.

25. The compound of claim 2 which is 9α-fluoro-11β-hydroxy-3-oxo-17aα-propionyloxy-D-homoandrosta-1,4-diene-17aβ-carboxylic acid.

26. The compound of claim 2 which is 11β-hydroxy-17aα-propionyloxy-3-oxo-D-homoandrost-4-ene-17aβ-carboxylic acid chloromethyl ester.

27. The compound of claim 2 which is 11β-hydroxy-17aα-propionyloxy-3-oxo-D-homoandrost-4-ene-17aβ-carboxylic acid fluoromethyl ester.

28. The compound of claim 2 which is 6α-fluoro-11β-hydroxy-3-oxo-17aα-propionyloxy-D-homoandrost-4-ene-17aβ-carboxylic acid methyl ester.

29. The compound of claim 2 which is 17aα-acetoxy-11β-hydroxy-6α-methyl-3-oxo-D-homoandrost-4-ene-17aβ-carboxylic acid methyl ester.

30. A compound of claim 1 wherein $R^9$ is hydrogen, fluorine or chlorine.

31. The compound of claim 30 which is 17aα-acetoxy-9α,11β-dichloro-3-oxo-D-homoandrost-4-ene-17aβ-carboxylic acid methyl ester.

32. The compound of claim 30 which is 17aα-acetoxy-9α-chloro-11β-fluoro-3-oxo-D-homoandrosta-1,4-diene-17aβ-carboxylic acid methyl ester.

33. The compound of claim 30 which is 9α,11β-dichloro-17aα-hydroxy-3-oxo-D-homoandrost-4-ene-17aβ-carboxylic acid.

34. The compound of claim 30 which is 9α,11β-dichloro-17aα-hydroxy-3-oxo-D-homoandrosta-1,4-diene-17aβ-carboxylic acid.

35. The compound of claim 30 which is 6α,9α-dichloro-11β-fluoro-17aα-hydroxy-3-oxo-D-homoandrost-4-ene-17aβ-carboxylic acid.

36. A compound of claim 1 wherein the broken line in the 1,2-position is a carbon-carbon bond.

37. The compound of claim 36 which is 6α,9α-dichloro-11β-fluoro-17aα-hydroxy-3-oxo-D-homoandrosta-1,4-diene-17aβ-carboxylic acid.

38. The compound of claim 36 which is 17aα-acetoxy-9α-fluoro-11β-hydroxy-3-oxo-D-homoandrosta-1,4-diene-17aβ-carboxylic acid methyl ester.

39. The compound of claim 36 which is 6α,9-difluoro-11β, 17aα-dihydroxy-3-oxo-D-homoandrosta-1,4-diene-17aβ-carboxylic acid.

40. The compound of claim 36 which is 17aα-acetoxy-6α, 9α-difluoro-11β-hydroxy-3-oxo-D-homoandrosta-1,4-diene-17aβ-carboxylic acid.

41. The compound of claim 36 which is 17aα-acetoxy-6α, 9α-difluoro-11β-hydroxy-3-oxo-D-homoandrosta-1,4-diene-17aβ-carboxylic acid methyl ester.

42. The compound of claim 1 which is 3,11-dioxo-17aα-propionyloxy-D-homoandrost-4-ene-17aβ-carboxylic acid butyl ester.

43. The compound of claim 1 which is 17aα-acetoxy-3,11-dioxo-D-homoandrost-4-ene-17aβ-carboxylic acid methyl ester.

* * * * *